United States Patent [19]
Meshberg

[11] Patent Number: 5,516,006
[45] Date of Patent: May 14, 1996

[54] NASAL DISPENSER

[76] Inventor: Philip Meshberg, 2770 S. Ocean Blvd., Apartment 602, Palm Beach, Fla. 33480

[21] Appl. No.: 99,386

[22] Filed: Jul. 30, 1993

[51] Int. Cl.⁶ .......................................................... B67D 5/64
[52] U.S. Cl. ........................... 222/25; 222/162; 222/288; 222/309; 222/321.6; 222/183; 222/562
[58] Field of Search ............................ 222/43, 162, 309, 222/321, 182, 183, 190, 283, 288, 23, 25, 29, 282, 562, 386, 321.6; 128/200.14, 200.22, 200.23

[56] References Cited

U.S. PATENT DOCUMENTS

| | | | |
|---|---|---|---|
| 2,914,222 | 11/1959 | Meshberg | 222/162 |
| 2,966,283 | 12/1960 | Darvie | 222/162 X |
| 3,211,346 | 10/1965 | Meshberg | 222/263 |
| 3,254,803 | 6/1966 | Meshberg | 222/182 |
| 4,185,755 | 1/1980 | Sachs et al. | 222/309 X |
| 4,454,964 | 6/1984 | Sacher | 222/309 X |
| 4,463,880 | 8/1984 | Kramer et al. | 222/189 |
| 4,771,769 | 9/1988 | Hegemann et al. | 222/162 X |
| 4,871,092 | 10/1989 | Maerte | 222/309 X |
| 4,946,069 | 8/1990 | Fuchs | 222/43 |
| 5,152,435 | 10/1992 | Stand et al. | 222/321 |

FOREIGN PATENT DOCUMENTS

| | | |
|---|---|---|
| 0070385 | 1/1983 | European Pat. Off. . |
| 0098939 | 1/1984 | European Pat. Off. . |
| 0452728 | 10/1991 | European Pat. Off. . |
| 0509863 | 10/1992 | European Pat. Off. . |
| 2658486 | 8/1991 | France . |
| WO91/13689 | 9/1991 | WIPO . |
| WO92/00812 | 1/1992 | WIPO . |

*Primary Examiner*—Kevin P. Shaver
*Attorney, Agent, or Firm*—Kenyon & Kenyon

[57] ABSTRACT

The present invention relates to a dispenser for dispensing medications into the nostril. The device has a number of advantageous features. First, the device includes air grooves in the spray head to allow the drawing in of air into the nostril during dispensing, to assist in the intake of the dispensed medication. Second, the device contains a mechanism for varying the amount of the dose dispensed. This feature is advantageous in that it allows an accurate metered dose to be dispensed, while still allowing flexibility in the size of the dose dispensed. The device can also have indicia for indicating when the last dose was dispensed, and can include a disinfecting feature for the spray head. The device can also have a gripping feature which spaces the fingers from the nostril into which medication is dispensed.

10 Claims, 5 Drawing Sheets

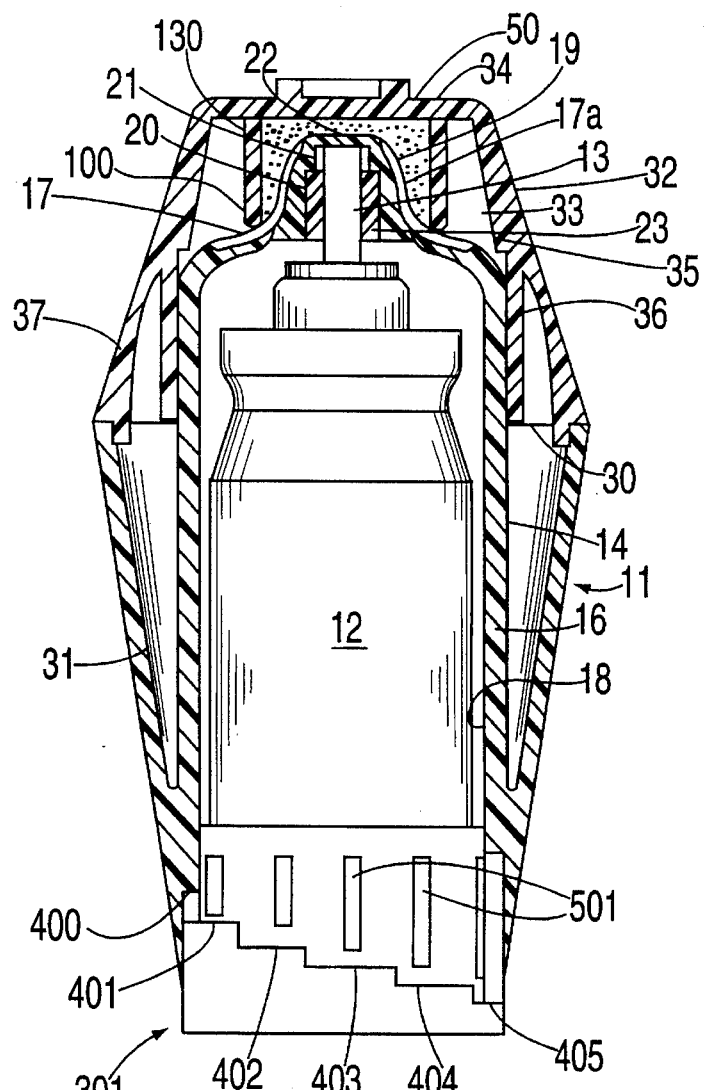
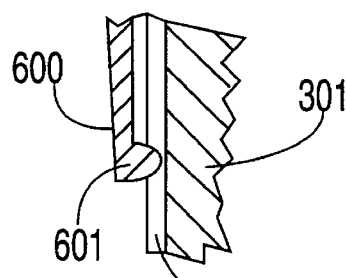
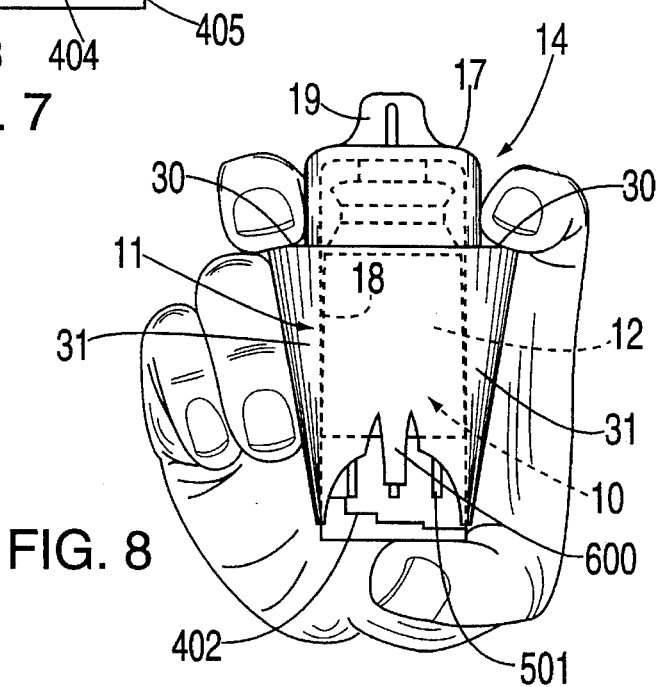
FIG. 7
FIG. 8a
FIG. 8

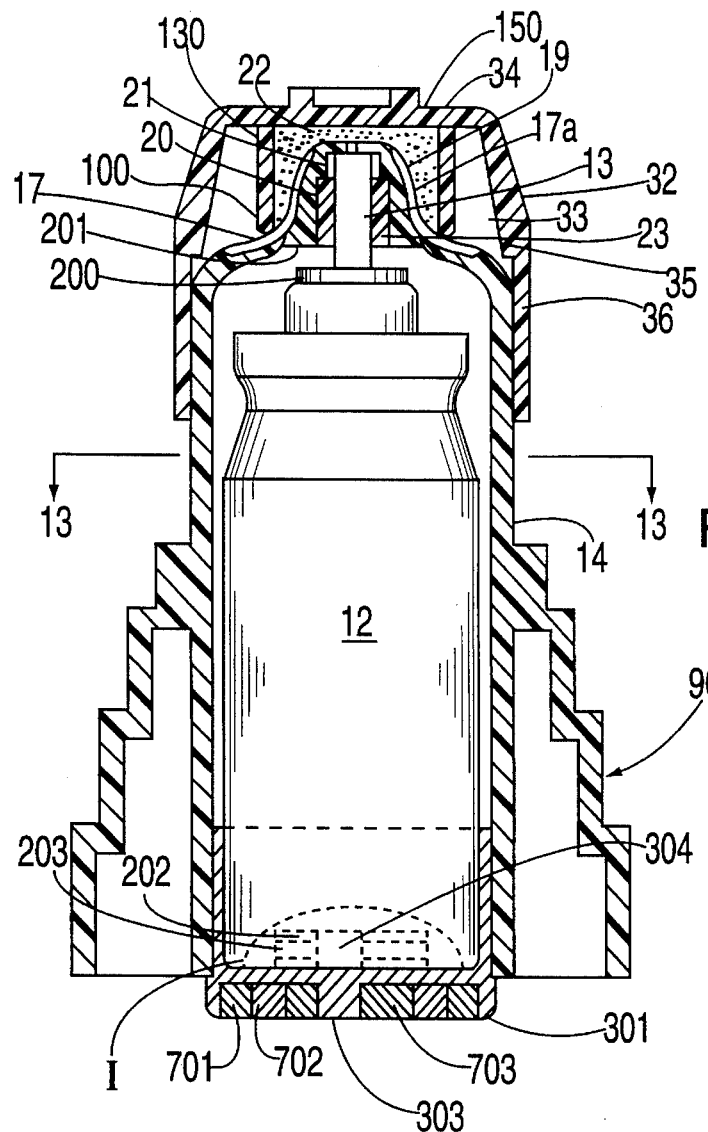
FIG. 11
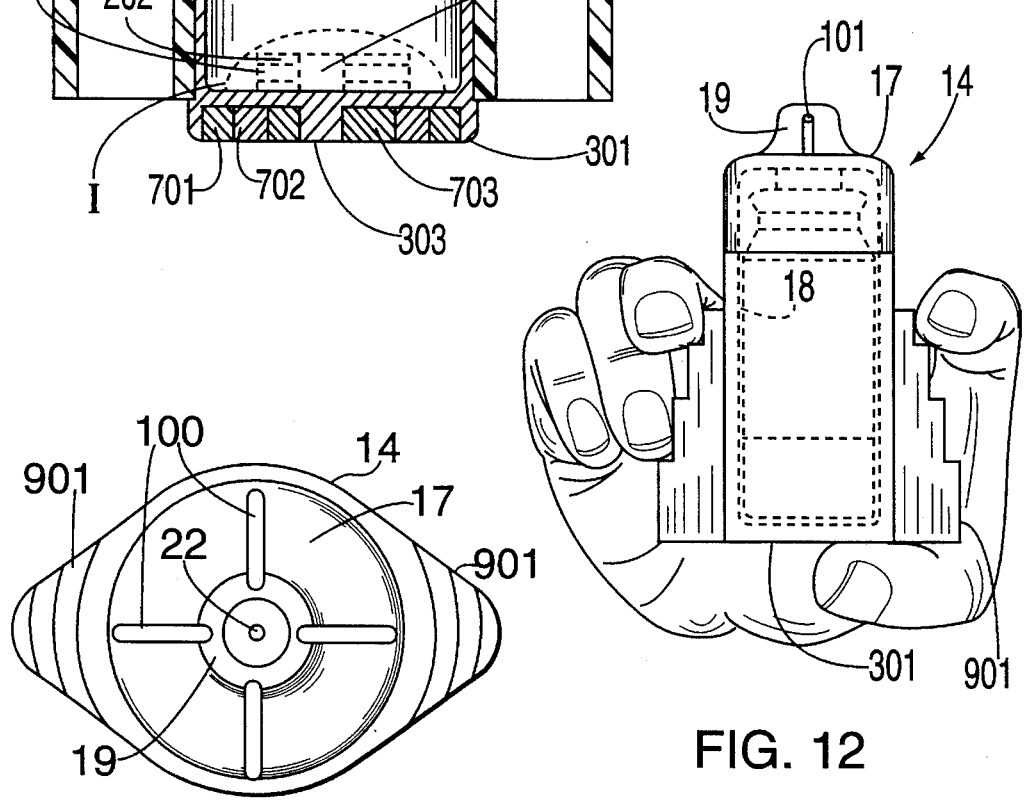
FIG. 12
FIG. 13

NASAL DISPENSER

BACKGROUND OF THE INVENTION

1. Field of the Invention

This invention relates to material dispensing devices of the types including a container for the material to be dispensed and relatively movable operating device projecting outwardly of the container for dispensing the material. More specifically, it pertains to a package for such a material dispensing device. The invention is particularly useful for dispensing medications in accurate metered quantities into the body, in the form of a spray, and allows an end user to adjust the quantity of material dispensed in each metered dose. One type of medication which the present invention is particularly useful for dispensing is insulin, which may be administered in accurate metered doses nasally with the device of the present invention.

2. Description of the Related Art

U.S. Pat. No. 3,254,803 shows a device for dispensing quantities of liquid in the form of a spray into a nasal cavity. The device of this patent uses an aerosol container mounted in a dispensing package for dispensing a metered quantity of liquid. The device of U.S. Pat. No. 3,254,803 does not, however, allow a user to select or vary the quantity of liquid delivered with each dose, since the amount delivered is dependant upon the structure of the metering valve within the aerosol container.

U.S. Pat. No. 3,211,346 shows a device for dispensing liquid under the action of a pump, in which the pump is mounted to a non-vented container pressurized by a quantity of inert gas. This type of device, in which the material to be dispensed does not come into contact with air until it exits the spray head, is particularly useful for dispensing medications, which could degrade if placed in contact with the air used to vent a conventional piston-operated dispensing pump. The device of U.S. Pat. No. 3,211,346 does not contain any mechanism for limiting the length of the stroke of the pump. The only metered quantity that this pump can dispense is that quantity that comes when the pump is depressed through its full stroke.

U.S. patent application Ser. Nos. 07/999,331 and 08/012,196 show mechanisms for limiting the length of stroke of a spray pump, to thereby allow the pump to dispense a number of different metered quantities. The devices of these patent applications are designed to be used with spray pump devices which use a finger-operated reciprocating actuator, and include mechanisms whereby a conventionally-styled actuator interacts with a stroke limiting device to control the amount of liquid dispensed. These devices also include different spray nozzles for different particle sizes, with differently structured break-up devices. The devices of these patent applications are not suited for a spray nozzle which is inserted nasally, since such devices do not use a conventionally-styled actuator.

SUMMARY OF THE INVENTION

It is an object of the invention to provide a package for a material dispensing device which facilitates the relative movement of a container for the material being dispensed and an operating member projecting from the container through which the material is dispensed.

It is also an object of the invention to provide a package for a material dispensing device, wherein the device comprises a container for the material having a relatively movable operating member projecting therefrom through which the material is dispensed, the package including a housing open at one end and providing a cavity for removably receiving the container, the housing being provided with a recess communicating the cavity outwardly of the housing and fictionally receiving and holding the operating member of device, the container being engageable through the open end of the housing or via a driving piston for imparting a force thereto for moving it in the housing relative to the operating member. The housing can have opposed outwardly flared walls formed integral with and of substantially the same thickness as the side walls, against which force may be applied in a direction opposed to the force applied to the container for relatively moving the container and operating member to dispense the material. As an alternative, the housing may have stepped projections depending therefrom for allowing the fingers to grip the housing and thereby allow dispensing of spray.

Another object of the invention is to provide a package for a material dispensing device including a container receiving housing and a removable cover member therefor. The cover member may have a disinfectant mechanism which contacts the spray nozzle every time the cover is placed on the housing, thereby preventing bacteria or other undesirable microorganisms from developing or growing on the spray nozzle.

Still another object of the invention is to provide a package for a material dispensing device which includes a mechanical breakup device in the path of the material being dispensed, the breakup device being locked within the confines of the package so that accidental displacement thereof is prevented.

Yet another object of the invention is to provide a nasal applicator package for a material dispensing device that facilitates the relative movement of the material container and operating member so that the material is dispensed. The nasal applicator package includes a mechanical breakup device for the material being dispensed, the breakup device being positioned adjacent and within the applicating nozzle and secured against accidental displacement therefrom during the dispensing operating.

It is further an object of the invention to provide a package for a device for dispensing materials using a reciprocating pump. The container and pump should be non-vented, to prevent the contact of air with the product to be dispensed within the container. By using a non-vented pump, the product to be dispensed is prevented from being degraded by contact with air in the container. The use of a pump allows the adjustment, through suitable stop mechanisms, to control the length of stroke of the pump, and thereby the amount of the dose dispensed with each actuation of the pump. The container includes a pump stem projecting from the container through which material is dispensed. The package includes a housing open at one end and having a side wall portion of substantially uniform thickness and a closed end portion. The container is adapted to be removably received in the housing with the pump stem frictionally retained and held in a recess formed in the closed end portion. The housing has a bore therethrough for receiving the pump stem and providing a passage through which the material is dispensed. The container is engageable through the open end of the housing by either direct finger pressure or finger pressure on a driving piston mechanism for applying a force thereto for moving the container relative to the pump stem. The side wall portion of the housing is formed with opposed integral flared walls projecting outwardly from the housing, or with stepped portions projecting outwardly therefrom, of substantially the same thickness as the side wall portions. These projecting portions are used to provide an opposing force to the finger force used to actuate the pump.

It is still further an object of the invention to provide a package for material dispensing device which adapted to be manufactured by quantity production methods, is readily assembled with the device and is of such rugged character it will functions over long periods of time with freedom from all difficulties.

It is another object of the invention to provide a nasal dispenser which allows the drawing in of air through the nose during dispensing to assist in the inhalation of medication. It is another object of the invention to provide a dispenser with indicia for indicating the size, time and date of the last dispensed dose. It is another object of the present invention to provide a dispenser which allows the fingers to be kept away from the nostril during dispensing, and which allows the easy disinfecting of the spray nozzle between use.

DESCRIPTION OF THE DRAWINGS

Other objects and advantages of the invention will be apparent from the specification and claims, when considered in connection with the attached sheets of drawings, illustrating one form of the invention, wherein like characters represent like parts and in which:

FIG. 7 is an elevational view, in section, of a package according to a second embodiment of the invention in combination with a material dispensing device;

FIG. 8 is an elevational view of the dispensing package of FIG. 7, showing the material dispensing device in dotted lines, being manually operated as contemplated by the invention;

FIG. 8a is a cross-sectional view of the rotational detent used in the dispensing device of FIG. 7;

FIG. 11 is an elevational view, in section, of a package according to a third embodiment of the invention in combination with a material dispensing device;

FIG. 12 is an elevational view of the dispensing package of FIG. 11, showing the material dispensing device in dotted lines, being manually operated as contemplated by the invention.

FIG. 13 is a view, taken in the direction of the arrows 13—13 in FIG. 11, of the dispensing package of FIG. 11;

Detailed Description of the Invention

Figure 1:
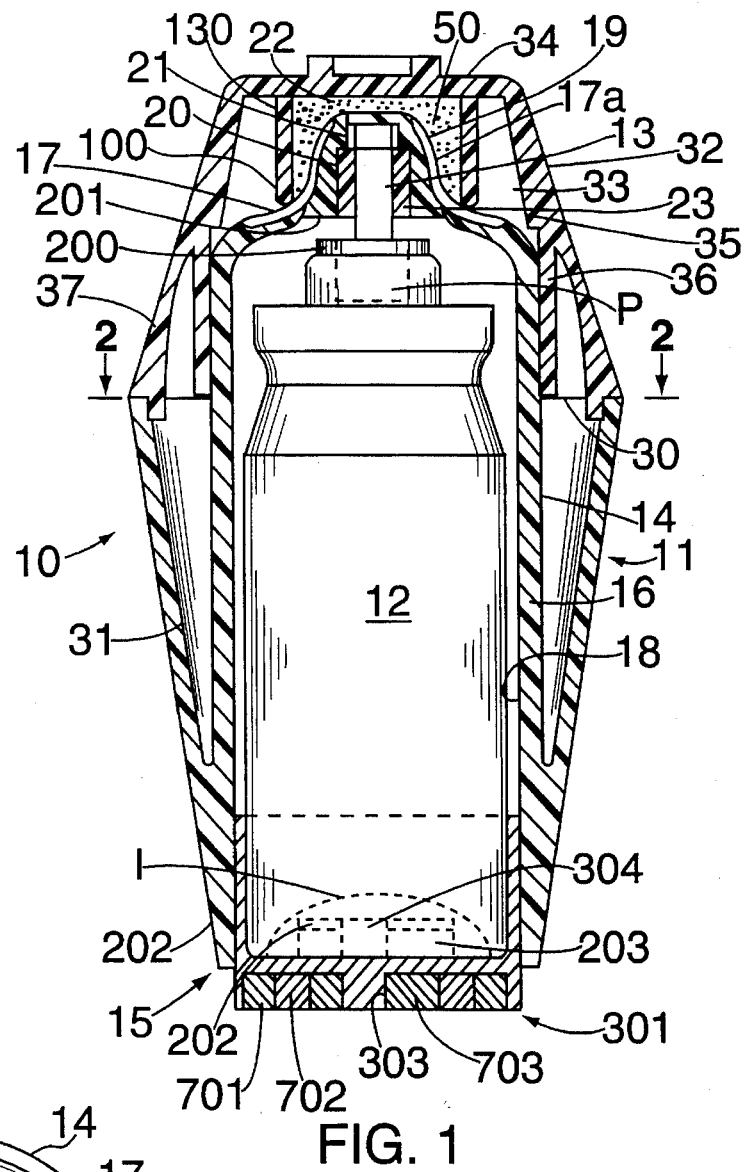
FIG. 1 is an elevational view, in section, of a package according to a first embodiment of the invention in combination with a material dispensing device.
Figure 2:
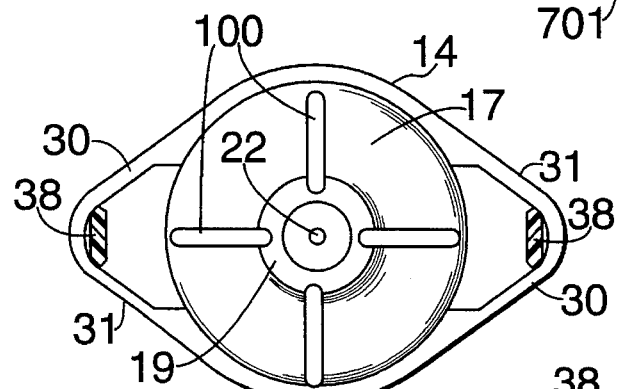
FIG. 2 is a view, taken in the direction of the arrows 2—2 in FIG. 1, of the dispensing package of FIG. 1.
Figure 4:
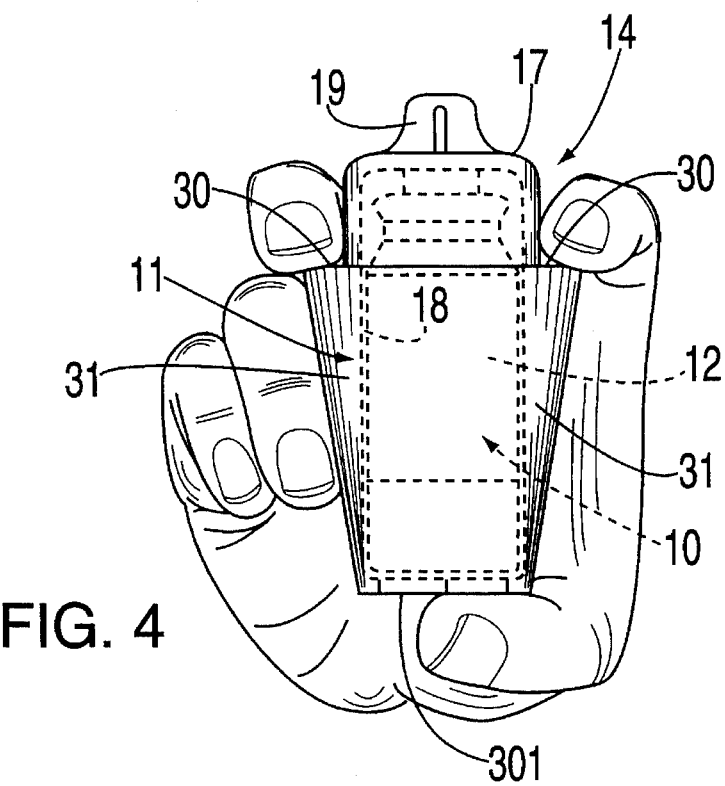
FIG. 4 is an elevational view of the dispensing package of FIG. 1, showing the material dispensing device in dotted lines, being manually operated as contemplated by the invention.

Referring now to the drawings for a more detailed description of the invention, the FIGS. 1 and 4 a material dispensing device 10 is shown in combination with the invention, for protecting the dispensing device and facilitating its operation.

While the packaging concepts of the present invention are applicable to a variety of dispensing devices, which include a container for the material to be dispensed and a dispensing operating member connected thereto, in the herein illustrated form of the invention the device 10 comprises a well know type of material dispensing package including a pump P and non-vented container 12 (i.e., like the pump and container shown in U.S. Pat. No. 3,211,346) having a reciprocable operating member or pump stem 13 projecting outwardly of the container for operating the pump on being moved relative thereto, the operating member being formed with an axial passage (also not shown) through which the material is dispensed. The container 12 is preferably filled with a medication which may enter the blood stream when dispensed into the nasal cavity, for example, a medication like insulin.

It is common practice in the material dispensing art, and particularly in the field of spray pump devices, to package the dispensing device for decorative or protective reasons. In most material dispensing devices, spraying is initiated by displacement of an actuator by finger pressure. In certain devices, however, such a nasal applicators, or the like, an actuator may not be used, since the spray nozzle is inserted in the nasal passage. In such a device, another mechanism must be provided for operating the device.

The dispensing package 11, according to the present invention, in addition to forming the conventional decorative and protective casing for the device 10, provides the mechanism for relatively moving the material container 12 and its dispensing pump stem 13 to operate the device.

As illustrated, the package 11, which may be molded or similarly formed from plastic or like material and is inserted into a nasal passage, includes a housing 14, open at one end as at 15, having a cylindrical side wall portion 16 of the substantially uniform thickness and closed end portion 17. The side wall portion and closed end portion define within the housing a cavity 18 that substantially conforms in shape to the outline of material container 12 and is adapted to movably receive the container therein. As clearly shown in FIG. 4, the container is engageable through the opposite end 15 of the housing for applying a force thereto, as by thumb pressure or the like, for moving the container in the cavity. The thumb pressure could be applied directly to the container 12, or as shown in FIG. 4, could be applied to a driving piston 301 slidable in the open end 15 of the housing.

The closed end portion 17 of the housing 14 is formed with recess 17a provides communication between the cavity 18 and the exterior of the housing. The recess is adapted to receive and frictionally retain the operating member 13 of the dispensing device 10 so that the passage communicates with the exterior of the housing and the pump stem 13 is held in position relative to the package 11. While the closed end portion 17 of the housing and the recess 17a therein may take many forms, depending upon the ultimate use of the device 10, in the herein illustrated form of the invention the closed end portion is formed with a boss 19, providing a nozzle or applicator tip for insertion into a nasal passage, and the recess includes a passage extending through the boss 19. The boss 19 is shaped so as to limit the amount of penetration of the boss 19 into the nasal passage. The boss 19 may advantageously include one or more air grooves 100 channeled in the surface of the boss 19. The air grooves 100 allow the user to draw in air through the nose as material is being dispensed from the package 10, thereby assisting in the delivery of the medication in container 12 to the bloodstream of the individual user.

While it is within the concepts of the invention for the recess 17a to comprise merely a bore of uniform diameter extending through the closed end portion of the housing for providing the passage for fictionally receiving the operating member of the dispensing device, in the nasal applicator illustrated, where it is desirable to diffuse or break up the body of material being dispensed the recess includes a plurality of axially aligned communicating bores 20, 21 communicating with a bore 22 in an outer wall of the portion 17, said bores 20, 21 being adapted to receive and fictionally hold a mechanical breakup device 23, the bore 24 of which receives the operating member 13 and provides passage through which the material is dispensed.

Figure 5:
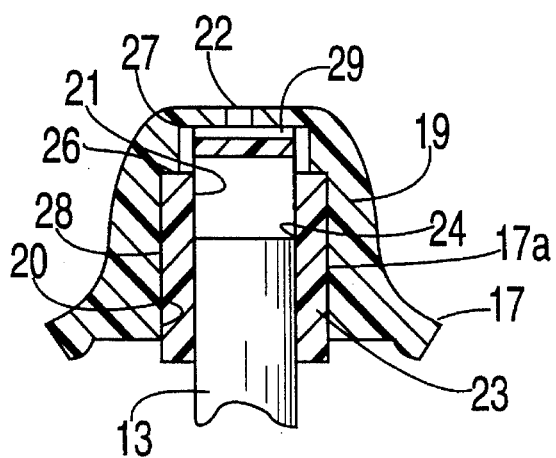
FIG. 5 is a fragmentary elevational view, in section, of the nasal applicator end of the dispensing package of FIG. 1.
Figure 6:
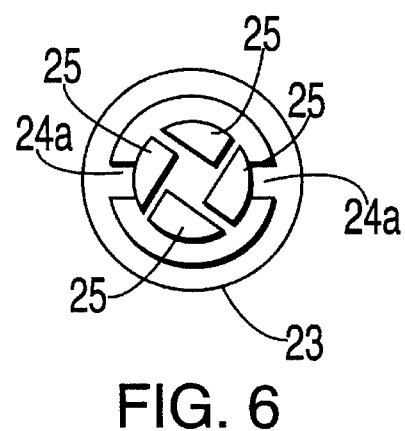
FIG. 6 is an end view of the mechanical breakup device embodied in the end of the dispensing device shown in the FIG. 5.

The mechanical breakup device 23, which may take any form well known to the art, but preferably has its passage 24 interrupt by baffles, 25 or the like for providing a tortuous path 24a for breaking up the material being dispensed, is locked in the recess 17a to prevent its accidental displacement and discharge into the nasal passage during the dispensing operation. As illustrated most clearly in FIG. 5, the mechanical breakup device 23 is locked in the recess by forming the axially aligned bores 20, 21 and 22 of reduced diameter relative to one another, progressing from the cavity 18 outwardly, thereby providing shoulders 26 and 27 against which shoulders 28 and 29, formed on the breakup device, abut.

In order to dispense the material from the container 12, by relatively moving the container and the housing carrying the dispensing operating member 13, shoulders 30 are provided on opposite sides of the housing against which a force, such as finger pressure, may be applied—as shown in FIG. 4—in a direction opposed to the force moving the container through the open end 15 of the housing. While the shoulders 30 may be provided in any known manner and take any desired form, in one form of the invention illustrated they comprise outwardly flared wall portions 31. It will be noted that the outwardly flared wall portions 31, which have their sides gently tapering into the surface of the housing side wall portion 16, are of substantially the same thickness as the side wall portion to eliminate strains and the like when the dispensing package is manufactured by a molding operation or the like.

Figure 3:
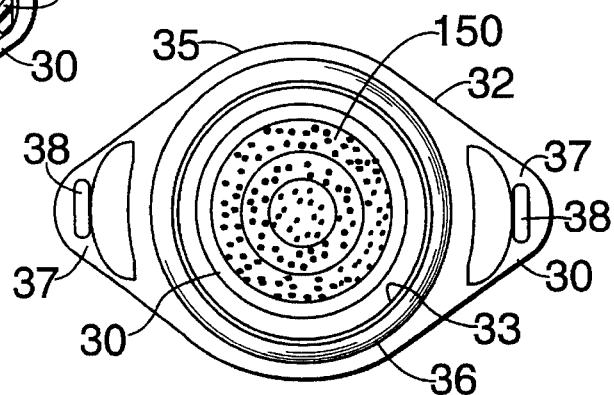
FIG. 3 is bottom view of the cover member of the dispensing package of FIG. 1.

In order to complete the dispensing package 11 and protect the boss 19 when the applicator is not in use, a removable cover member 32 is provided as shown in FIGS. 1 and 3. The cover member, which may be formed of the same material and in a manner similar to the package housing 14 and defines a chamber 33 for receiving the closed end portion of the housing, has an end wall 34 and a side wall portion 35, the latter including a depending annular skirt 36 for fictionally receiving a portion of the housing side wall and holding the cover member in place. In a manner similar to that described in connection with package housing, the cover member 32 is formed with opposed outwardly flared wall portions 37, which are adapted to complement and abut the shoulders 30 of the housing for providing a symmetrical appearance to the overall package and close the pockets formed by the housing shoulders. Depending projections 38, formed integral with outwardly flared portions 37 of the cover member, engage the shoulder 30 of the housing and extend into the pockets formed thereby for preventing the cover member form turning relative to the housing. The cover member 32 may include a device for disinfecting the boss 19 to prevent the spread and growth of microorganisms on the boss 19 between use. The disinfecting device includes a flange 130 depending downwardly from the cover member 32, which flange holds an absorbent material 150 (e.g., a sponge-like synthetic material) which can be impregnated with a liquid disinfectant. The absorbent material 150 is shaped and positioned so that when the cover member 32 is placed on the dispensing package 11, is surrounds and contacts the boss 19, thereby allowing the disinfectant in the absorbent material 150 to contact the boss 19.

The device of FIG. 1 includes a mechanism for limiting the stroke of the pump piston (not shown) within the container 12. A removable stop device 200, in the form of a rigid plastic washer, is placed upon the pump stem 13. The stop device 200 is therefore positioned such that it will contact the top surface of the container 12, and as the container 12 is pushed upwardly, a stop surface 201 on the closed end portion 17. When the top of the stop device 200 contacts the stop surface 201, it prevents further upward movement of the container 12, thereby limiting the stroke of the pump in the container 12, and therefore the amount of the material dispensed. The amount of material dispensed, as a function of the length of the stroke of the pump, will be controlled by the thickness of the stop device 200. In order to allow the user to vary the amount of material dispensed with a particular spray, a plurality of stop devices 202, 203 can further be provided, each of the stop devices 200, 202, 203 having a different thickness to provide a different dose size. The stop devices 200, 202, 203 can be of different colors, so that they can be easily distinguished and the various dose sizes that they provide can be determined from a quick visual inspection. The additional stop devices can be stored on a hub 304 on the driving piston 301 for easy access and storage. This hub 304 can project into an indentation I in the container 12.

FIGS. 7 and 8 show a second embodiment of the present invention, wherein similar elements in the second embodiment to those shown in the first embodiment of FIGS. 1–6 are labelled with the same reference numerals. The embodiment of FIGS. 7 and 8 uses a different stroke limiting device than that shown in the embodiment of FIGS. 1–6. The driving piston 301 in the second embodiment includes a series of inwardly facing stop surfaces 401–405 which extend inwardly at a series of different elevations. The housing side wall portion 16 includes a outwardly facing stop surface 400 which interacts with one of the stop surfaces 401–405 to stop further upward movement of the driving piston 301. Which stop surface 401–405 with which the stop surface 400 interacts is dependent upon the rotational orientation of the driving piston 301. The stop surface 400 extends for only a certain circumferential extent on the housing side wall portion 16; the remaining circumferential extent of the housing side wall portion 16 allows free movement of the driving piston 301 into the interior of the package housing 14.

In order to accurately align the driving piston 301 with the proper stop surface 401–405 so as to interact with the stop surface 400, the driving piston contains a series of alignment grooves 501 oriented above the stop surfaces 401–405. A detent 600 with a radially inwardly facing tab 601 which interacts with the grooves 501 acts to lock the driving piston 301 into a particular rotational orientation. The radially inwardly facing tab 601 on the detent 600 slides in the grooves 501 when the driving piston 301 is actuated. In order to change the rotational alignment of the driving piston 301, the detent 600, which is resiliently biased, is pulled radially outwardly so that the tab 601 and groove 501 are disengaged, and the driving piston 301 is rotated until the tab 601 snaps into the desired groove 501.

Figure 9:
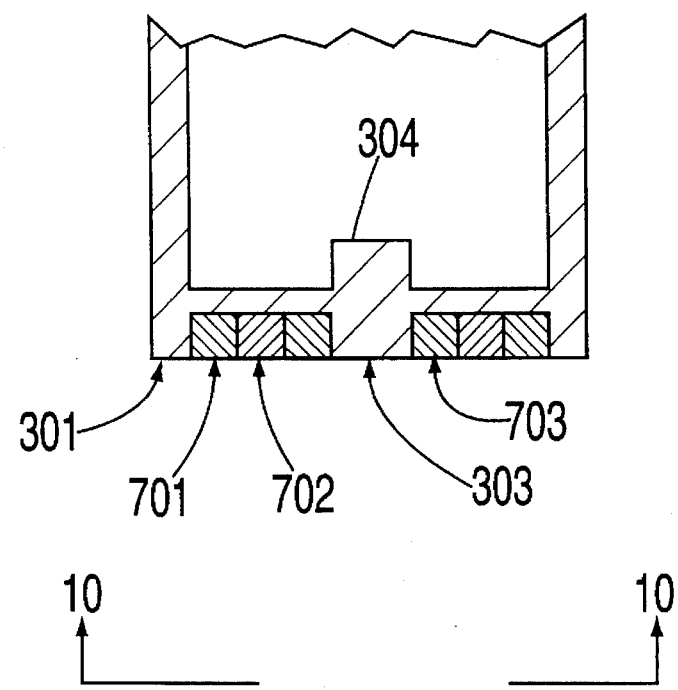
FIG. 9 is a cross-sectional view of a second embodiment of the driving piston of the present invention, which includes indicia for dose and date.
Figure 10:
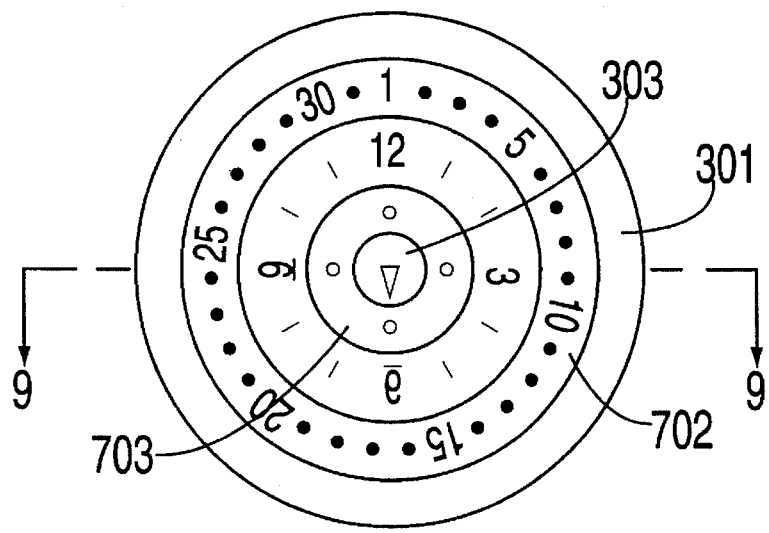
FIG. 10 is a bottom view of the driving piston of FIG. 9.

FIGS. 9 and 10 show an alternative embodiment of the driving piston 301 which may be used in either the embodiments of FIGS. 1 or 7 (the stop surfaces of the FIG. 7 driving piston are not shown merely for ease of illustration). This driving piston 301 includes an indicia mechanism for indicating to the user the size, time and date of the last dose dispensed. A hub 303 is contained on the driving piston 301, the hub 303 mounting a series of indicia rings 701–703. Ring 703 can have a series of colored dots to indicate the size of dose last dispensed, which dots can be aligned with a fixed indicia on the hub 303. Rings 702 and 701 can respectively contain rings displaying time and date of last dose, with the indicia being alignable with a fixed indicia on the hub 303. Rings 701–703 and hub 303 can have interlocking detents between them to allow the indicia to be snapped into a particular alignment and prevent unwanted rotation.

FIGS. 11–13 show a third embodiment of the present invention, with a alternate mechanism for gripping and actuating the device. The structure and operation of the device, other than the gripping mechanism described below, can be in accordance with either the embodiments of FIGS. 1 or 7. The package housing 14 has depending therefrom a pair of radially projecting steps 901 extending on opposite sides of the housing 14. As can be seen particularly in FIG. 12, the fingers grip these steps 901 to allow actuation of the spray pump in the container 12. The embodiment of FIGS. 11–13 is advantageous in that the fingers are spaced a distance farther away from the nostril, allowing easier insertion of the device into the nostril for subsequent dispensing.

Thus, among others, the various objects and advantages of the invention as aforenoted have been achieved. Obviously, numerous changes in constructions may be resorted to without departing from he concepts of the invention as defined in the claims.

I claim:

1. A device for dispensing metered quantities of material as either liquid or spray comprising:

a container holding a quantity of material to be dispensed:

a pump for dispensing material from an interior of said container, said pump including a pump stem for delivering liquid from said pump to an exterior of said container;

a housing, said container being mounted for reciprocal movement in said housing, said housing including a spray passage, said pump stem engaging said spray passage;

a pump stroke limiting device, said pump stroke limiting device being mounted between said container and said housing, said pump stroke limiting device limiting an amount of reciprocal movement of said container in said housing to thereby control a length of stroke of said pump, said pump stroke limiting device comprising a plurality of elements, each said element being of a different configuration than any other said element, said elements being adapted for mounting on said pump stem, one of said elements interacting with a portion of said container adjacent said pump stem and a portion of said housing adjacent said pump stem when mounted on said pump stem, to thereby limit an amount of reciprocal movement of said container in said housing; and a driving piston connected to said container and mounted for reciprocal movement in said housing, whereby force applied to said driving piston reciprocates said container in said housing, said driving piston comprising indicia for indicating the time, date, and quantity of the last dispensed dose, said driving piston further comprising a hub and said indicia comprises a plurality of rotatable rings mounted on said hub.

2. A device for dispensing metered quantities of material as either liquid or spray comprising:

a container holding a quantity of material to be dispensed, said container further comprising a pump for dispensing material from an interior of said container, said pump including a pump stem for delivering liquid from said pump to an exterior of said container;

a housing, said container being mounted for reciprocal movement in said housing, said housing including a spray passage, said pump stem engaging said spray passage;

a pump stroke limiting device, said pump stroke limiting device being mounted between said container and said housing, said pump stroke limiting device limiting an amount of reciprocal movement of said container in said housing to thereby control a length of stroke of said pump; and a driving piston connected to said container and mounted for reciprocal movement in said housing, whereby force applied to said driving piston reciprocates said container in said housing, said driving piston comprising indicia for indicating a time, date, and quantity of a last dispensed dose, said driving piston comprising a hub and said indicia comprising a plurality of rotatable rings mounted on said hub.

3. A device for dispensing metered quantities of material as either liquid or spray comprising:

a container holding a quantity of material to be dispensed;

a pump for dispensing material from an interior of said container, said pump including a pump stem for delivering liquid from said pump to an exterior of said container;

a housing, said container being mounted for reciprocal movement in said housing, said housing including a spray passage, said pump stem engaging said spray passage;

a pump stroke limiting device, said pump stroke limiting device being mounted between said container and said housing, said pump stroke limiting device limiting an amount of reciprocal movement of said container in said housing to thereby control a length of stroke of said pump, said pump stroke limiting device comprising a plurality of elements, each said element being of a different configuration than any other said element, said elements being adapted for mounting on said pump stem, one of said elements interacting with a portion of said container adjacent said pump stem and a portion of said housing adjacent said pump stem when mounted on said pump stem, to thereby limit an amount of reciprocal movement of said container in said housing; and a driving piston connected to said container and mounted for reciprocal movement in said housing, whereby force applied to said driving piston reciprocates said container in said housing; and a plurality of said elements, said elements being stored on said driving piston.

4. A device for dispensing metered quantities of material as either liquid or spray comprising:

a container holding a quantity of material to be dispensed, said container further comprising a pump for dispensing material from an interior of said container, said pump including a pump stem for delivering liquid from said pump to an exterior of said container;

a housing, said container being mounted for reciprocal movement in said housing, said housing including a spray passage, said pump stem engaging said spray passage;

a pump stroke limiting device, said pump stroke limiting device being mounted between said container and said housing, said pump stroke limiting device limiting an amount of reciprocal movement of said container in said housing to thereby control a length of stroke of said pump, said pump stroke limiting device comprising an element adapted for mounting on said pump stem, said element interacting with a portion of said container adjacent said pump stem and a portion of said housing adjacent said pump stem to thereby limit an amount of reciprocal movement of said container in said housing;

a driving piston connected to said container and mounted for reciprocal movement in said housing, whereby force applied to said driving piston reciprocates said container in said housing; and a plurality of said elements, said elements being stored on said driving piston.

5. The device of claim 4, wherein:

said housing further comprises a spray nozzle, said spray nozzle communicating with said spray passage.

6. The device of claim 5, wherein:

said spray nozzle further comprises at least one air passage on an axially outward surface.

7. The device of claim 5 further comprising:

a cover, said cover being attachable to said housing to thereby cover said spray nozzle.

8. The device of claim 7, wherein:

said cover comprises a disinfecting device for providing disinfectant to the said spray nozzle when said cover is attached to said housing.

9. The device of claim 4, wherein:

said housing comprises at least one axially upwardly facing flange to provide a surface for the application of a force opposite to said force applied to said driving piston.

10. The device of claim 9, wherein:

said at least one axially outwardly facing flange comprises a plurality of stepped flanges.

* * * * *